US010912866B2

(12) United States Patent
Zhang et al.

(10) Patent No.: US 10,912,866 B2
(45) Date of Patent: Feb. 9, 2021

(54) POROUS BIONIC SKULL REPAIRING MATERIAL, PREPARATION METHOD AND IMPLEMENT METHOD THEREOF

(71) Applicant: Shandong Branden Medical Device Co., Ltd, Shandong (CN)

(72) Inventors: Haijun Zhang, Shandong (CN); Liming Liu, Shandong (CN); Shoutao Lu, Shandong (CN); Wenrui Cao, Shandong (CN); Hairong Xu, Shandong (CN); Chao Zhou, Shandong (CN); Yuxia Yin, Shandong (CN); Wenbo Hou, Shandong (CN); Cuihai Duan, Shandong (CN); Guang Liu, Shandong (CN)

(73) Assignee: Shandong Branden Medical Device Co., Ltd, Shandong (CN)

( * ) Notice: Subject to any disclaimer, the term of this patent is extended or adjusted under 35 U.S.C. 154(b) by 62 days.

(21) Appl. No.: 16/233,117

(22) Filed: Dec. 27, 2018

(65) Prior Publication Data

US 2019/0201584 A1 Jul. 4, 2019

(30) Foreign Application Priority Data

Jan. 2, 2018 (CN) .......................... 2018 1 0000736

(51) Int. Cl.
*A61L 27/46* (2006.01)
*A61L 27/56* (2006.01)
(Continued)

(52) U.S. Cl.
CPC .............. *A61L 27/56* (2013.01); *A61L 27/18* (2013.01); *A61L 27/26* (2013.01); *A61L 27/365* (2013.01);
(Continued)

(58) Field of Classification Search
CPC .. A61F 2/28; A61F 2/30; A61F 2/2875; A61F 2/2803; A61F 2/3099; A61L 27/56; A61L 27/46; A61L 27/18
See application file for complete search history.

(56) References Cited

U.S. PATENT DOCUMENTS

2012/0128739 A1* 5/2012 Nygaard ................ A61L 27/56
424/400
2013/0171443 A1 7/2013 Morrissette et al.
(Continued)

FOREIGN PATENT DOCUMENTS

CN 104667345 6/2015
CN 106178104 12/2016

OTHER PUBLICATIONS

Susan Liao, "Research on Mineralized Collagen Base Tissue-Engineered Bone Material", Thesis of Doctoral Degree, The Department of Materials Science and Engineering Tsinghua University, Apr. 2003, pp. 1-112.

*Primary Examiner* — Jason-Dennis N Stewart
(74) *Attorney, Agent, or Firm* — JCIPRNET (57) ABSTRACT

A porous bionic skull repairing material includes a polymer material, whose structure is consistent with that of a human skull. The surface layers of the porous bionic skull repairing material are dense layers which are composed of non-degradable or degradable polymer materials and has blind holes having an asymmetric structure, and the inner layer of the porous bionic skull repairing material is a loose layer which has a porous structure. The repairing material can be molded by adopting a mixed mould pressing method or a 3D printing method, simulates a bone structure, with two dense sides and a loose middle, of a human skull to the greatest extent.

11 Claims, 2 Drawing Sheets

(51) Int. Cl.
*A61L 27/18* (2006.01)
*A61L 27/26* (2006.01)
*A61L 27/36* (2006.01)
*A61L 27/48* (2006.01)
*B32B 5/14* (2006.01)
*A61F 2/28* (2006.01)
*B32B 5/22* (2006.01)

(52) U.S. Cl.
CPC ............... *A61L 27/46* (2013.01); *A61L 27/48* (2013.01); *B32B 5/145* (2013.01); *A61F 2002/2817* (2013.01); *A61L 2400/08* (2013.01); *A61L 2430/02* (2013.01); *B32B 5/22* (2013.01)

(56) References Cited

U.S. PATENT DOCUMENTS

| | | | |
|---|---|---|---|
| 2013/0190882 A1* | 7/2013 | Humphrey | A61F 2/4014 623/19.14 |
| 2014/0088716 A1* | 3/2014 | Zubok | A61F 2/30 623/18.11 |
| 2016/0262894 A1* | 9/2016 | Cronstein | A61F 2/28 |

* cited by examiner

POROUS BIONIC SKULL REPAIRING MATERIAL, PREPARATION METHOD AND IMPLEMENT METHOD THEREOF

CROSS-REFERENCE TO RELATED APPLICATION

This application claims the priority benefit of China application serial no. 201810000736.7, filed on Jan. 2, 2018. The entirety of the above-mentioned patent application is hereby incorporated by reference herein and made a part of this specification.

BACKGROUND OF THE INVENTION

Technical Field

The disclosure belongs to the fields of polymer materials and biomedical engineering, and particularly relates to a bionic skull repairing material with multiple pores and a personalized preparation method thereof as well as an implement method thereof as a bionic skull repairing prosthesis.

Description of Related Art

According to statistical data, there are over three million patients with skull defects caused by traffic accidents and accidents in China yearly, and there are over 2.8 million people to be treated in hospital in America yearly due to craniocerebral injury. Skull defect is one of common problems in neurosurgery department, and mainly results from burning, craniocerebral trauma, intracranial infection, tumor operation, skull reduced pressure surgery and the like. For craniocerebral injury having a diameter of more than 3 mm, it is needed to perform skull repairing surgery in order to maintain closure of a cranial cavity, shape and repair appearance of a patient, maintain the stability of physiological intracranial pressure, relieve blood-supply disorder and abnormal cerebrospinal fluid cycle caused by skull defect, and the like.

Common materials for skull repairing mainly include autogenous bones and artificial materials, organic glass, bone cement, silicone rubber, stainless steel and titanium meshes, polyetheretherketone and the like, but the above materials can only take a partial function replacement effect, among them, polyetheretherketone (PEEK) is a repairing material whose elasticity modulus is closest to human bones at present and becomes a focus of skull repairing research at present. Polyetheretherketone has the advantages of good biocompatibility, excellent mechanical property, light weight and the like and meanwhile has X-ray penetrability, but PEEK itself is an inert material and has a problem of poor osteointegration, thereby limiting its application in skull repairing to a certain extent. In the prior art, there are relevant reports that the osteointegration of the PEEK material is improved by carrying out abrasive blasting and plasma spraying on the surface of a PEEK substrate or adding bioactive substances into the PEEK substrate or other manners, but the above methods only improve the osteointegration of PEEK to the moderate extent and still have the problems of potential layering, poor stability and poor mechanical property.

An ideal skull repairing material requires reasonable space structure, porosity and connectivity, preferably, is consistent with a bone structure, has good mechanical property, has an effect of fusing with tissues for a long term, and can be perfectly matched with the defect part of the patient. However, the skull repairing prosthesis prepared by various method at this stage is far worse than the ideal skull repairing material. The porous bionic skull repairing material provided by the following solutions of the disclosure has good performances either in structure, mechanical property and osteointegration, or in matching.

American patent US 2013/0171443A1 discloses a porous polymer material and a preparation method thereof. A porous PEEK implant is prepared by a compression molding process, which has no bionic structure with dense two sides and loose middle, and has no bioactive substances and an antibacterial coating on the porous surface.

Chinese patent CN 106178104A discloses medical drug-loading porous polyetheretherketone and a preparation method thereof. Porous polyetheretherketone is prepared by pressure casting and chemical corrosion. This method just describes a molding manner of porous polyetheretherketone and does not involve a molding method of a prosthesis having a complicated structure.

Chinese patent CN 104667345A discloses a skull repairing prosthesis having bioactivity and a preparation method thereof. This skull repairing prosthesis consists of a polyaryletherketone layer, an irradiation layer and a nano fiber membrane layer. The three-layer skull structure prepared by using this method is different from structures of human cortical bones and cancellous bones.

In an academic paper "RESEARCH ON MINERALIZED COLLAGEN BASE TISSUE-ENGINEERED BONE MATERIAL", Liao Susan proposes that strength is enhanced through mineralization on collagen, and an osteogenesis structure of a bone tissue cancellous bone is simulated. However, as a hard tissue repairing material, it still has the disadvantages of poor mechanical property and too fast degradation speed.

It can be seen that the existing skull repairing prosthesis has the shortages of poor skull matching, large difference from a natural skull structure, poor fusion with tissue for a long term and the like.

SUMMARY OF THE INVENTION

The objective of the disclosure is to provide a porous bionic skull repairing material. This repairing material is highly matched with a defect part of a patient, has a bionic structure having two dense sides and a loose middle and can ensure good mechanical property, the middle part of the repairing material has a mutually crossed or three-dimensional porous structure which is capable of providing a microenvironment of bone tissue growth and proliferation. This repairing material has good performances either in structure, mechanical property and osteointegration, or in matching.

The porous bionic skull repairing material provided by the disclosure, from inner to outer, successively includes an inner dense layer, a loose layer and an outer dense layer, wherein, the loose layer is located between the inner dense layer and the outer dense layer, and the inner dense layer and the outer dense layer are both lightly connected with the loose layer.

Further, the inner dense layer and the outer dense layer of the above porous bionic skull repairing material have high mechanical strength, and the inner dense layer and the outer dense layer are both provided with asymmetrical blind hole structures; preferably, a diameter of each of the blind hole structures is 0.1 mm-10 mm, a gap between the blind hole structures is 1 mm-10 mm; the size and gap of the blind hole structures are adjusted according to the volume of subcutaneous hydrops, thereby greatly reducing a contact area between a tissue and the repairing material, decreasing subcutaneous hydrops and lowering the occurrence rate of infection.

Further, the loose layer of the above porous bionic skull repairing material is of a porous structure with a pore size of 10-700±m and a porosity of 5%-90%. The pore diameter shape and size of the loose layer can be adjusted according to added different porogens and contents of porogens. Preferably, the porous structure of the loose layer is a crossed pore-shaped structure or a three-dimensional porous structure.

Further, in the above porous bionic skull repairing material, the inner dense layer and the outer dense layer simulate a cortical bone structure, and the loose layer simulates a skull bone trabecula structure. The whole porous bionic skull repairing material is matched with a human skull structure.

Preferably, the thickness of the inner dense layer is 0.5-3 mm, the thickness of the outer dense layer is 0.5-3 mm, and the thickness of the loose layer is 0.5-4 mm. These thicknesses can be adjusted according to a specific bionic human bone structure under the practical situation.

Further, in the above porous bionic skull repairing material, the inner dense layer and the outer dense layer are made of polymer materials, or a mixture of a polymer material and a bioactive substance, wherein, the materials of the inner dense layer and the outer dense layer can be the same or different. The loose layer is made of a mixture of a polymer material and a porogen, or made of a mixture of a polymer material, a porogen and a bioactive substance. The inner and outer dense layers contain no porogen, are dense in structure, have high mechanical strength and biocompatibility, and is similar to a human cortical bone in structure. The loose layer has a porous structure which is similar to a human skull bone trabecula structure. The pore surface of the porous structure of the loose layer is prone to attaching bioactive substances, thereby facilitating the bone tissue to grow from the side of the porous bionic skull repairing material and to fuse with the tissue for a long term.

Further, the above polymer material is a non-degradable polymer material or a degradable polymer material. The above non-degradable polymer material is a polyaryletherketone material which is a crystallized polymer formed by connecting phenylene with ketone via an ether bond, comprising at least one of polyetheretherketone (PEEK), polyetherketone (PEK), polyetherketoneketone (PEKK), polyetheretherketoneketone (PEEKK) and polyetherketoneetherketoneketone (PEKEKK). The degradable polymer material is a polyester degradable polymer material which is a general term of polymers formed by polycondensation of polyol and polyatomic acid, comprising at least one of polylactic acid, polyglycollide and polycaprolactone. When the porous bionic skull repairing material is used for adults, the non-degradable polymer material is generally selected, and when the porous bionic skull repairing material is used for crowds whose bones are not shaped, such as children, the degradable polymer material is generally selected.

Further, the bioactive substance is at least one of nano hydroxyapatite (HAp), nano titania (TiO$_2$), calcium silicate, β-tricalcium phosphate and bioactive glass. The bioactive substance is beneficial to repairing and regeneration of bone cells, and is also beneficial to long-term fusion of the porous bionic repairing material and tissues. When the inner and outer dense layers or the loose layer contains the bioactive substance, preferably, the amount of the bioactive substances is 5%~15% of mass of the polymer material in this layer.

Further, the porogen is an inorganic salt or a metal wire, the inorganic salt forms a three-dimensional porous structure and the metal wire forms a crossed pore-shaped structure. Preferably, the inorganic salt is a water-soluble inorganic salt that is easy to remove, a positive ion is preferably a sodium ion or/and a potassium ion, a negative ion is at least one of a chlorine ion, a carbonate ion, a sulfate ion, a phosphate ion and a nitrate ion, more preferably, the inorganic salt is at least one of sodium chloride, sodium carbonate, potassium chloride, potassium sulfate, potassium carbonate and potassium phosphate. Preferably, the metal wire is a metal wire that is easily removed using acid, more preferably, is formed by winding at least one of a magnesium wire, a zinc wire and an aluminum wire. The shape and size of the pore can be controlled according to a winding manner and a winding degree of the metal wire.

Further, the above porous bionic skull repairing material also contains an antibacterial component or an active factor, or simultaneously contains the antibacterial component and the active factor, the antibacterial component or the active factor is beneficial to long-term fusion of an artificial skull and prevention of infection. Where, the antibacterial component and/or the active factor is located on at least one of the inner dense layer, the outer dense layer and the loose layer, for example, can be located on any layer, or any two layers, or three layers at the same time, preferably, on three layers at the same time. Where, when being present in the inner dense layer or the outer dense layer, the antibacterial component or/and the active factor are only located on the naked surface of the inner dense layer or the outer dense layer due to dense structures of inner and outer dense layers; when being present in the loose layer, the antibacterial component or/and the active factor are located not only on the naked surface of the loose layer but also in the pores inside the loose layer (that is to say, located on the pore surface of the inside of the loose layer) due to a fact that the inside of the loose layer is porous.

Further, the antibacterial component is at least one of a metal substance, a non-metal substance and an organic substance, the metal substance is at least one of a silver ion, a zinc ion, a copper ion, silver oxide, zinc oxide and copper oxide, the non-metal substance is a compound containing at least one of a hydrogen element, a chlorine element and a selenium element and having an antibacterial action, and the organic substance is at least one of antibiotics, antimicrobial peptide and chitosan. The active factor is at least one of a bone Gla protein (BGP), a bone morphogenetic protein (BMP) and a basic fibroblast growth factor (BFGF). The contents of the antibacterial component and the active factor can be adjusted according to the practical situation.

Further, the above porous bionic skull repairing material can be subjected to surface modification, which can further improve properties of the porous bionic skull repairing material, such as bioactivity and antibacterial property, by virtue of one or more of the following a-g manners:

a. treating the porous bionic skull repairing material with a gas cluster ion beam method;

b. treating the porous bionic skull repairing material with a plasma method;

c. treating the porous bionic skull repairing material with a surface covering method;

d. treating the porous bionic skull repairing material with a laser irradiation method;

e. treating the porous bionic skull repairing material with an electron beam deposition method;

f. treating the porous bionic skull repairing material with an embedding method; and g. treating the porous bionic skull repairing material with an osmose method.

Further, the gas cluster ion beam method is a method for preparing a film utilizing special properties of cluster particles, for example, surface treatment is carried out on the repairing material using gas cluster ion beams to enhance adhesion and proliferation capabilities of cells. The plasma method refers to precipitating one layer of molten or semi-molten metal or non-metal coating on the surface of the porous bionic skull repairing material, for example, one layer of HA coating is sprayed on the inner and outer dense layers adopting a plasma method. The laser irradiation method refers to changing the surface property of the porous bionic skull repairing material from biological inertia to bioactivity through photoinduced oxidation under the participation of oxygen. The electron beam deposition method is a universal method for preparing a uniform coating at room temperature, for example, a titanium metal coating is prepared on the surface of the porous bionic skull repairing material adopting the electron beam deposition method. The embedding method refers to immobilizing enzyme or cells in a three-dimensional mesh-shaped structure of a polymer compound, for example, tobramycin is loaded into the pores of the repairing material adopting the embedding method.

Further, the above porous bionic skull repairing material of the disclosure simulates the human skull structure, can be used as bionic skull repairing prosthesis, has good mechanical property, good biocompatibility and good skull matching, and is capable of being fused with tissues for a long term, so properties are excellent. Thus, an implement method of the porous bionic skull repairing material as the porous bionic skull repairing prosthesis is also included in the protection scope of the disclosure. The porous bionic skull repairing prosthesis is suitable for skull defect caused by external force, congenital skull defect or skull defect caused by diseases, and especially, has a good effect on repairing of skull defect and tissue regeneration.

Further, the disclosure also provides a preparation method of the above porous bionic skull repairing material. The porous bionic skull repairing material is prepared by using a mixed mould pressing method or a 3D printing technology. According to the specific situation of the skull defect of a patient, the personalized custom-made porous bionic skull repairing material matched with the skull defect can be achieved.

Preferably, the disclosure provides a mixed mould pressing preparation method of the above porous bionic skull repairing material, including the following steps: firstly, carrying out cold pressing on a raw material to form a clod pressed board including an outer dense layer, a loose layer and an inner dense layer, then carrying out heat melting and hot pressing to form a hot pressed board, and shaping the hot pressed board to gain a size and a curvature which are matched with a skull defect part of a patient through a moldless forming technique so as to obtain the porous bionic skull repairing material.

Further, the above preparation method also comprises a step of removing a porogen in the shaped board, namely, after the hot pressed board is shaped through the moldless forming technique to gain a size and a curvature which are matched with the skull defect part of the patient, removing the porogen in the shaped board so as to obtain the porous bionic skull repairing material.

Further, the porogen in the shaped board is removed utilizing at least one of ultrasonic water bath, constant temperature oscillator, salt bath and acid etching.

Preferably, after the porogen in the material is removed, the above preparation method also includes a step of carrying out surface modification on the porous bionic skull repairing material using at least one of a gas cluster ion beam method, a plasma method, a surface covering method, a laser irradiation method, an electron beam deposition method, an embedding method and an osmose method.

Preferably, after the porogen in the material is removed, the above preparation method also includes a step of putting the porous bionic skull repairing material into a feed liquid containing an antibacterial component and/or an active factor so that the porous bionic skull repairing material contains the antibacterial component and/or the active factor, wherein, after the porogen is removed, the material is adhered with only the antibacterial component and/or the active factor, and can also be subjected to surface modification, or both at the same time. When they are both carried out at the same time, generally, surface modification is carried out at first, and then the antibacterial component and/or the active factor are added.

Further, when in cold pressing, raw materials of the outer dense layer, the loose layer and the inner dense layer are added into a mould in sequence for once or multi-time cold pressing, so as to form a board in which inner and outer layers are the dense layers and a middle layer is the loose layer.

Further, in the above preparation method, when in cold pressing, various raw materials are compacted at a pressure of 1-150 MPa to prepare the cold pressed board, pressurizing and pressure releasing are repeatedly carried out once or more than once so that the residual gas in the mould is discharged, the pressure is gradually raised when in pressurizing, a set pressure is reached and then maintained for 1-60 min. The pressure and time for cold pressing are related to the formation thickness of the board, and can be adjusted according to actual demand. When in cold pressing, the shape of the mould is designed so that required blind hole structures are formed on the inner and outer dense layers.

Further, in the above preparation method, raw materials of the inner dense layer and the outer dense layer are polymer materials or a mixture of a polymer material and a bioactive substance; the raw materials of the loose layer is a mixture of a polymer material and a porogen or a mixture of a polymer material, a porogen and a bioactive substance. When heat melting and hot pressing are carried out, the temperature is set between the melting point of the polymer material and the melting point of the porogen; the residual gas is completely discharged, subsequently, the materials of the cold pressed board are quickly placed in a hydraulic machine for hot pressing, a pressure is set as 1-100 MPa, pressurizing and pressure releasing are repeatedly carried out once or more than once, the pressure is gradually raised when in pressurizing, and a set pressure is reached and maintained for 1-60 min. The pressure and time for hot pressing are related to the formation thickness of the board and can be adjusted according to actual demand.

Figure 3:
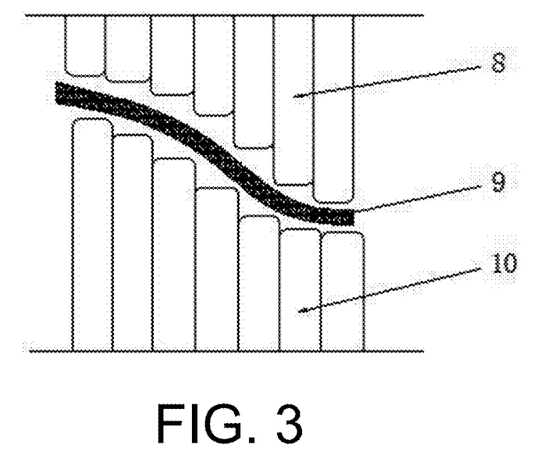
FIG. 3 is a plastic formation diagram of a board through a moldless forming technique when in mixed mould pressing.

Further, in the above preparation method, when moldless formation is carried out, a blank obtained by hot pressing is heated to be between the plastic deformation temperature and the melting point of the polymer material, and then the hot pressed board is compacted and molded utilizing a moldless forming technique according to a three-dimensional model rebuilt at a skull defect part of a patient, as shown in FIG. 3.

Further, a method for preparing the porous bionic skull repairing material or the porous bionic skull repairing prosthesis using the above mixed mould pressing method (also referred to as a mixed pressing method) specifically includes the following steps:

(1) scanning a skull of a patient using a computed tomography technology, dividing and extracting data utilizing image processing software, rebuilding a three-dimensional model for a skull and a defect part of a patient, and calculating the size and curvature of the artificial skull of the defect part.

(2) preparing a board with a composite structure:

preparing a mixed powder material: respectively preparing raw materials of the inner dense layer, the outer dense layer and the loose layer in a certain proportion with a polymer material, a bioactive substance and a porogen as raw materials;

cold pressing molding: preparing raw materials of inner and outer dense layers and the loose layer in an ideal volume of a 102% mould: placing the inner and outer dense layer powder materials and the loose layer powder material prepared in the above step into the mould, placing the mould into a hydraulic machine to compact the materials at a pressure of 1-150 MPa to prepare the board, wherein, pressurizing and pressure releasing are repeatedly carried out once or more than once, the pressure is gradually raised when in pressurizing so that the residual gas in the mould is completely discharged, and a set pressure is reached and then maintained for 1-60 min, so as to ensure the quality and property of the board;

melting: turning on an external heating device on the mould containing a pressed blank obtained in the above step or placing the mould into a high-temperature oven for heat melting of the board, wherein, the heating temperature is set between the boiling point of the polymer material and the melting point of the porogen, preferably, when the polymer material is a polyaryletherketone material, the temperature is set as 390-420° C., and heating time is more than 1 h;

hot pressing molding: quickly placing the mould containing the molten board blank obtained in the above step into a press machine, with a set pressure of 1-100 PMa, wherein, pressurizing and pressure releasing are repeatedly carried out once or more than once, the pressure is gradually raised when in pressurizing, and a set pressure is reached and then maintained for 1-60 min; after hot pressing, cooling the mould, and putting the cooled mould into a demould seat to be demouled and take out the blank when the temperature is reduced to 150° C. or below;

(3) shaping: guiding the built three-dimensional model for the skull defect part of the patient into moldless multi-point molding equipment, heating the blank obtained in the above step to be between a plastic deformation temperature and a melting point of the polymer material, quickly transferring the heated blank to the moldless multi-point molding equipment, pressing and molding to obtain the personalized skull repairing material customized according to the patient, and cutting the skull repairing material so that its size exceeds the size of calculated artificial skull by about 1 cm;

(4) preparing the porous bionic skull repairing prosthesis: placing the personalized skull repairing prosthesis obtained in the above step into an ultrasonic water bath pot or a constant-temperature oscillator or a salt bath pot or acid, with a set temperature of 50-100° C.; completely separating out the porogen, and subsequently, drying (for about 24 h) to obtain the porous bionic skull repairing prosthesis customized according to the patient.

Preferably, the disclosure also provides a 3D printing preparation method of the above porous bionic skull repairing material (namely the porous bionic skull repairing prosthesis), specifically comprising the following steps:

(1) scanning a skull of a patient using a computed tomography technology, dividing and extracting data utilizing image processing software, rebuilding a three-dimensional model for a skull and a defect part of a patient, and calculating the size and curvature of the artificial skull of the defect part;

(2) using polymer materials or a mixture of a polymer material and a bioactive substance as a raw material for 3D printing; and (3) printing the porous bionic skull repairing prosthesis utilizing a CT rebuilt model and a 3D printing technology according to the three-dimensional model for the skull defect part in the step (1).

Further, when in 3D printing, the raw materials used by various-layer structures of the porous bionic skull repairing prosthesis can be the same or different.

Compared with the prior art, the disclosure has the beneficial effects that:

1. The porous bionic skull repairing material provided by the disclosure can be used as a skull repairing prosthesis, its structure is matched with a human skull structure, surface layers are dense layers and an inner layer is a loose layer, so that a bone structure in which a human skull is dense in two sides and loose in the middle is highly simulated; the surface dense layer has high mechanical strength, the inner loose layer has a three-dimensional or crossed porous structure, and the surface of the pore can be adhered with a bioactive substance, thereby facilitating adhesion and proliferation of osteoblasts and meanwhile facilitating bone tissues to grow from the side of the prosthesis and to fuse with tissues for a long term.

2. The porous skull repairing prosthesis provided by the disclosure can be subjected to surface modification by adopting multiple methods such as a gas cluster ion beam method, a plasma method, a surface covering method, a laser irradiation method, an electron beam deposition method, an embedding method and an osmose method, and can also be adhered with an antibacterial component and an active factor so that the obtained prosthesis has good mechanical property, bioactivity and infection resistance.

3. The materials of the skull repairing prosthesis provided by the disclosure are non-metal materials, and the weight and modulus of the prosthesis are closer to those of a human bone and do not bring discomfort for a patient. Furthermore, the skull repairing prosthesis is good in adiabaticity and does not damage the brain tissue of the patient due to fever. Moreover, the skull repairing prosthesis has good biocompatibility and bioactivity, and therefore has good safety and effectiveness after being implanted into a body.

4. For the porous bionic skull repairing prosthesis provided by the disclosure, the pores of the loose layer can be formed by the porogen, the porogen can select inorganic salts, and the shape and size of the pore can be adjusted according to the shape and size of the porogen particle.

5. For the porous bionic skull repairing prosthesis provided by the disclosure, the porogen on the loose layer can select metal materials, and the size of the pore can be adjusted according to the diameter of the metal material.

6. For the porous bionic skull repairing prosthesis provided by the disclosure, inner and outer dense layers of the prosthesis have asymmetrical blind hole structures, and thus a contact area between the tissue and the repairing prosthesis is reduced; the size of the blind pore and the size of a gap between the blind hole structures can be adjusted according to the volume of subcutaneous hydrops, and thus the subcutaneous hydrops and the occurrence rate infection can be greatly reduced.

7. The porous bionic skull repairing prosthesis provided by the disclosure can be molded by adopting a mixed mould pressing or 3D printing method, and the cost of the mixed mould pressing method is low relative to the 3D printing method. The porous bionic skull repairing prosthesis is customized according to the patient, so the matching degree is high, repairing of the skull is facilitated until complete fusion is achieved, and therefore the prosthesis has a good application prospect in the skull. In addition, the technology of the disclosure provides a good thought for maxillofacial bones, vertebra bones and limb bones.

BRIEF DESCRIPTION OF THE DRAWINGS

In the drawings, 1—outer dense layer; 2—loose layer; 3—inner dense layer; 4—core bar; 5—mould barrel; 6—demould seat; 7—base mould; 8—upper basic body of moldless multi-point molding equipment; 9—porous bionic skull repairing material; 10—lower basic body of moldless multi-point molding equipment.

DESCRIPTION OF THE EMBODIMENTS

Next, embodiments of the disclosure are further described in detail in combination with accompanying drawings. It should be understood that these embodiments are used for illustrating the disclosure but not limiting the scope of the disclosure. Implementation conditions adopted in examples can be further regulated according to conditions of specific manufacturers, non-noted implementation conditions are generally conditions in conventional experiments.

Example 1

1. A skull of a patient is scanned by using a computed tomography technology, a scanned image is stored in a DICOM (Digital Imaging and Communication in Medicine) format, data is divided and extracted utilizing image processing software, a three-dimensional model for a skull and a defect part of a patient is rebuilt, and the size and curvature of the artificial skull of the defect part are calculated.

Figure 1:
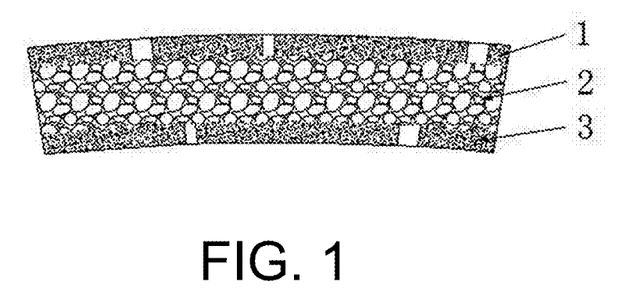
FIG. 1 is a structural diagram of a porous bionic skull repairing material.
Figure 2:
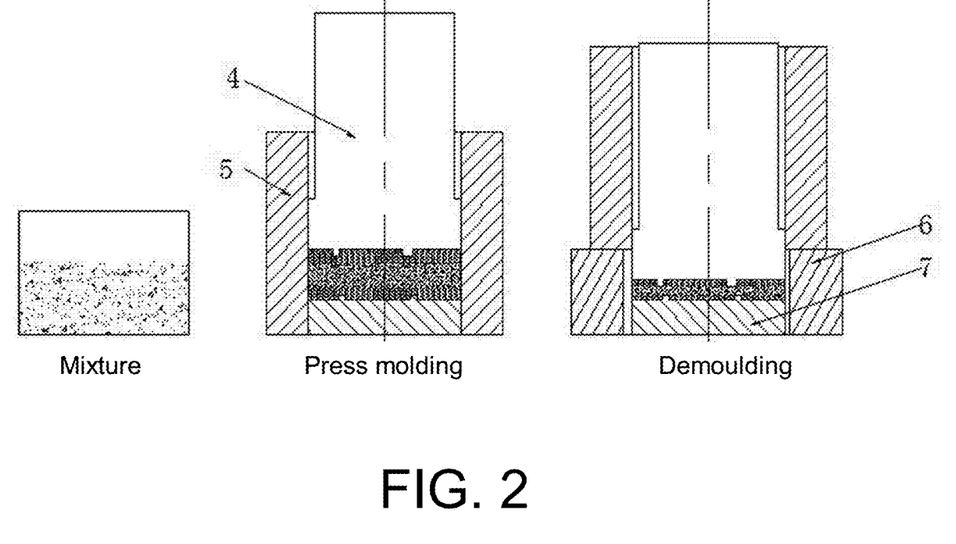
FIG. 2 is a formation diagram of a board when in mixed mould pressing

2. Preparation of a board:

preparation of mixed powder: a loose layer mixed powder material is prepared in an ideal volume of 102% mould, namely, NaCl particles having a size of 250 μm and PEEK powder having a grain size of 70 μm are sufficiently mixed for 30 min with a planet ball mill at 200 rpm in a ratio of PEEK to NaCl of 80 wt %:20 wt % to prepare a mixed powder material as the loose layer mixed powder material; and the dense layer powder material is pure PEEK powder;

preparation of a cold pressed sheet: the pure PEEK powder is poured into the bottom of the mould to be used as the inner dense layer, the loose layer mixed powder material is placed in the middle of the mould, then a layer of pure PEEK powder is paved on an upper layer to be used as the outer dense layer, the ready mould is placed in a hydraulic machine to compact the materials at a pressure of 30 MPa, pressurizing and pressure releasing are repeatedly carried out three times, the pressure is gradually raised when in pressurizing so that the residual gas in the mould is discharged, and the pressure is maintained for 5 min when achieving 30 Mpa, so as to ensure the quality and property of the product;

melting: the cold pressed mould is placed on a high-temperature oven or an external heating device for melting and heating the material at a heating temperature of 390° C. but less than a boiling point of the porogen NaCl, so that PEEK is completely molten, wherein, heating time is 1 h;

hot pressing: the mould in which the material is completely molten is quickly placed into a hydraulic machine for hot pressing, with a maximal set pressure of 15 MPa; pressurizing and pressure releasing are repeatedly carried out three times, the pressure is gradually raised when in pressurizing, and the pressure is maintained for 10 min after achieving 15 Mpa;

cooling: the pressure is released from the press machine when the temperature is reduced to less than 300° C. after the pressure is maintained, and the mould is cooled at a speed of 40° C./min; and demoulding: when the temperature of the mould is reduced to less than 150° C., demouling is carried out to prepare a board with inner and outer dense layers and a middle loose layer, as shown in FIG. 1, wherein, the inner and outer dense layers are both provided with blind hole structures whose pore size is 1 mm and a gap is 3 mm; the loose layer has three-dimensional pores with a pore size of 250 μm and a porosity of 20%; the thicknesses of the inner and outer dense layers are both 1.5 mm, and the thickness of the loose layer is 2 mm.

3. Plastic treatment: the built three-dimensional model for the skull defect part of the patient is guided into moldless multi-point molding equipment, the demoulded blank obtained in the above step is heated to 200° C., the heated blank is quickly transferred to the moldless multi-point molding equipment, compression molding is carried out to obtain the personalized skull repairing prosthesis customized according to the patient, and the skull repairing prosthesis is cut so that its size exceeds the size of calculated artificial skull by about 1 cm.

4. Preparation of a personalized porous bionic skull repairing prosthesis: the personalized skull repairing prosthesis obtained in the above step is placed into an ultrasonic water bath pot with a set temperature of 80° C. until the porogen is completely separated out, and subsequently, drying is carried out (for about 24 h) to obtain the porous bionic skull repairing prosthesis customized according to the patient.

a. Mechanical Property Test

The porous bionic skull repairing prosthesis obtained in step 4 is tested according to a method stipulated by GB/T1040.1-2006. Results are as follows:

| Yield strength (MPa) | Elongation ratio at breaking (%) | Elasticity modulus (GPa) |
| --- | --- | --- |
| 70 | 10.5 | 2.6 | b. Morphological Observation

Figure 4:
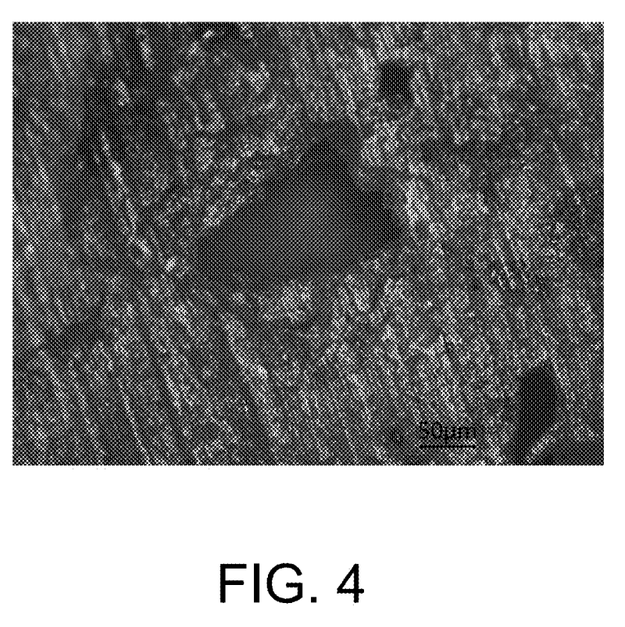
FIG. 4 is a local microcosmic enlarged view of a loose layer of a porous bionic skull repairing prosthesis prepared in example 1.

FIG. 4 is a local microcosmic enlarged view of the loose layer of the obtained porous bionic skull repairing prosthesis. It can be seen from the drawing that the loose layer has an obvious pore structure.

Example 2

1. A skull of a patient is scanned by using a computed tomography technology, a scanned image is stored in a DICOM (Digital Imaging and Communication in Medicine) format, data is divided and extracted utilizing image processing software, a three-dimensional model for a skull and a defect part of a patient is rebuilt, and the size and curvature of the artificial skull of the defect part are calculated.

2. Preparation of a board:

preparation of mixed powder: a mixed powder material of dense layers and a loose layer is prepared in an ideal volume of 102% mould, namely, NaCl particles having a size of 250 μm, PEEK powder having a grain size of 70 μm and nm-HA (nano hydroxyapatite) having a grain size of 70 nm are sufficiently mixed for 30 min with V-shaped blender mixer at 200 rpm in a ratio of PEEK to NaCl to nm-HA of 70 wt %:20 wt %:10 wt % to prepare a mixed powder material as a loose layer mixed powder material; and the dense layer powder material is pure PEEK powder;

preparation of a cold pressed sheet: the outer dense layer PEEK powder material is paved at the bottom of the mould, the loose layer mixed powder material is placed in the middle of the mould, then inner dense layer PEEK powder is paved on an upper layer, the ready mould is placed in a hydraulic machine to compact the materials at a pressure of 30 MPa, pressurizing and pressure releasing are repeatedly carried out three times so that the residual gas in the mould is completely discharged, the pressure is gradually raised when in pressurizing, and the pressure is maintained for 5 min when achieving 30 Mpa, so as to ensure the quality and property of the product;

melting: the cold pressed mould is placed on a high-temperature oven or an external heating device for melting and heating the material at a heating temperature of 400° C. but less than a boiling point of the porogen NaCl so that the PEEK powder is completely molten, wherein, heating time is 1 h;

hot pressing: the mould in which the material is completely molten is quickly placed into a hydraulic machine for hot pressing, with a maximal set pressure of 15 MPa; pressurizing and pressure releasing are repeatedly carried out three times, the pressure is gradually raised when in pressurizing, and the pressure is maintained for 10 min after achieving 15 Mpa;

cooling: the pressure is released from the press machine when the temperature is reduced to less than 300° C. after the pressure is maintained, and the mould is cooled at a speed of 40° C./min; and demoulding: when the temperature of the mould is reduced to less than 150° C., a blank is demoulded to take out a board; as shown in FIG. 1, the inner and outer dense layers are both provided with blind hole structures whose pore size is 1.5 mm and a gap is 3.5 mm; the loose layer has three-dimensional pores with a pore size of 250 μm and a porosity of 20%; the thicknesses of the inner and outer dense layers are 1.5 mm, and the thickness of the loose layer is 2 mm.

3. Plastic treatment: the built three-dimensional model for the skull defect part of the patient is guided into moldless multi-point molding equipment, the demoulded blank obtained in the above step is heated to 200° C., the heated blank is quickly transferred to the moldless multi-point molding equipment, compression molding is carried out to obtain the personalized skull repairing prosthesis customized according to the patient, and the skull repairing prosthesis is cut so that its size exceeds the size of calculated artificial skull by about 1 cm.

4. Preparation of a personalized porous bionic skull repairing prosthesis: the personalized skull repairing prosthesis obtained in the above step is placed into an ultrasonic water bath pot with a set temperature of 80° C. until the porogen is completely separated out, and subsequently, drying is carried out (for about 24 h) to obtain the porous bionic skull repairing prosthesis customized according to the patient.

a. Morphological Observation

Figure 5:
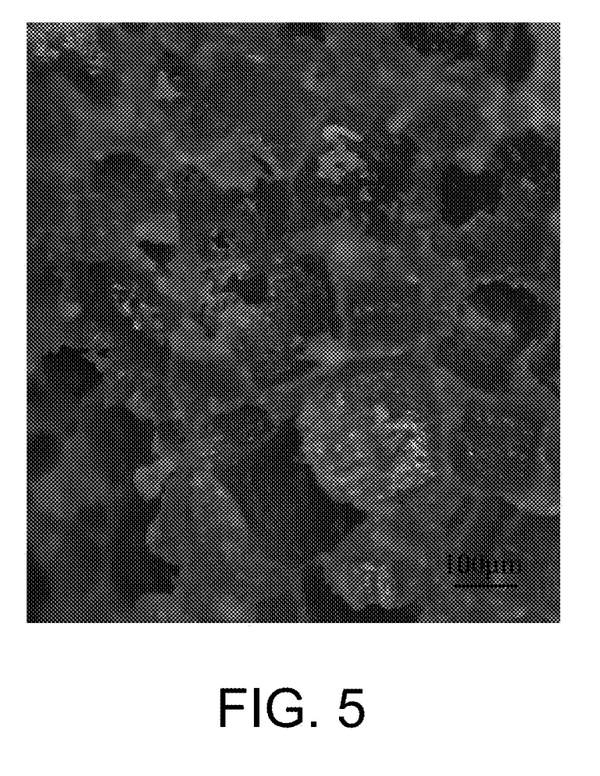
FIG. 5 is a local microcosmic enlarged view of a loose layer of a porous bionic skull repairing prosthesis prepared in example 2.

FIG. 5 is a local microcosmic enlarged view of the loose layer of the obtained porous bionic skull repairing prosthesis. It can be seen from the drawing that hydroxyapatite and polyetheretherketone have a good interface compatibility.

b. Mechanical Property Test

The porous bionic skull repairing prosthesis obtained in step 4 is tested according to a method stipulated by GB/T1040.1-2006. Results are as follows:

| Yield strength (MPa) | Elongation ratio at breaking (%) | Elasticity modulus (GPa) |
| --- | --- | --- |
| 85 | 10.5 | 2.8 |

Example 3

1. A skull of a patient is scanned by using a computed tomography technology, a scanned image is stored in a DICOM (Digital Imaging and Communication in Medicine) format, data is divided and extracted utilizing image processing software, a three-dimensional model for a skull and a defect part of a patient is rebuilt, and the size and curvature of the artificial skull of the defect part are calculated.

2. Preparation of a board:

preparation of mixed powder: a mixed powder material of dense layers and a loose layer is prepared in an ideal volume of 102% mould, namely, PEEK powder of 70 μm and $TiO_2$ of 70 nm are added into a V-shaped blender mixer in a ratio of PEEK to $TiO_2$ of 90 wt %:10 wt % to be sufficiently and evenly mixed to prepare a dense layer powder material; a mixed powder material is prepared from KCl particles having a size of 250 μm, PEEK powder having a grain size of 70 μm and $TiO_2$ powder of 70 nm are sufficiently mixed for 30 min with a planet ball mill at 200 rpm in a ratio of PEEK to KCl to $TiO_2$ of 65 wt %:25 wt %:10 wt % to prepare the loose layer mixed powder material;

preparation of a cold pressed sheet: the dense layer powder material is paved at the bottom of the mould, the loose layer mixed powder material is placed in the middle of the mould, the dense layer PEEK powder material is paved on an upper layer, the ready mould is placed in a hydraulic machine to compact the materials at a pressure of 30 MPa, pressurizing and pressure releasing are repeatedly carried out three times, the pressure is gradually raised when in pressurizing so that the residual gas in the mould is completely discharged, and the pressure is maintained for 4 min when achieving 30 Mpa, so as to ensure the quality and property of the product;

melting: the cold pressed mould is placed on a high-temperature oven or an external heating device for melting and heating the material at a heating temperature of 390° C. but less than a boiling point of KCl so that PEEK is completely molten, wherein, heating time is 45 min;

hot pressing: the mould in which the material is completely molten is quickly placed into a hydraulic machine for hot pressing, with a maximal set pressure of 15 MPa; pressurizing and pressure releasing are repeatedly carried out three times, the pressure is gradually raised when in pressurizing, and the pressure is maintained for 10 min after achieving 15 Mpa;

cooling: the pressure is released from the press machine when the temperature is reduced to less than 300° C. after the pressure is maintained, and the mould is cooled at a speed of 40° C./min; and demoulding: when the temperature of the mould is reduced to less than 150° C., a board is demoulded and taken out; the structure of the board is as shown in FIG. 1, wherein, the inner and outer dense layers are both provided with blind hole structures whose pore size is 1.5 mm and a gap is 4 mm; the loose layer has three-dimensional pores with a pore size of 250 μm and a porosity is 25%; the thicknesses of the inner and outer dense layers are 1 mm, and the thickness of the loose layer is 2 mm.

3. Plastic treatment: the built three-dimensional model for the skull defect part of the patient is guided into moldless multi-point molding equipment, the demoulded blank obtained in the above step is heated to 200° C., the heated blank is quickly transferred to the moldless multi-point molding equipment, compression molding is carried out to obtain the personalized skull repairing prosthesis customized according to the patient, and the skull repairing prosthesis is cut so that its size exceeds the size of calculated artificial skull by about 1 cm.

4. Preparation of a personalized porous bionic skull repairing prosthesis: the personalized skull repairing prosthesis obtained in the above step is placed into an ultrasonic water bath pot with a set temperature of 80° C. until the porogen is completely separated out, and subsequently, drying is carried out (for about 24 h) to obtain the porous bionic skull repairing prosthesis customized according to the patient.

5. The porous bionic skull repairing prosthesis in which the porogen is removed in the above step 4 is subjected to surface treatment using a gas cluster ion beam (GCIB) so as to improve the surface hydrophilicity of the prosthesis and facilitating adhesion of cells, thereby obtaining the porous bionic skull repairing prosthesis customized according to the patient.

a. Mechanical Property Test

The porous bionic skull repairing prosthesis obtained in step 5 is tested measured according to a method stipulated by GB/T1040.1-2006. Results are as follows:

| Yield strength (MPa) | Elongation ratio at breaking (%) | Elasticity modulus (GPa) |
|---|---|---|
| 72 | 9.8 | 2.2 |

Example 4

1. A skull of a patient is scanned by using a computed tomography technology, a scanned image is stored in a DICOM (Digital Imaging and Communication in Medicine) format, data is divided and extracted utilizing image processing software, a three-dimensional model for a skull and a defect part of a patient is rebuilt, and the size and curvature of the artificial skull of the defect part are calculated.

2. Preparation of a board:

preparation of mixed powder: a mixed powder material of dense layers and a loose layer is prepared in an ideal volume of 102% mould, namely, PEEK powder of 70 μm and hydroxyapatite powder of 70 nm are put into a V-shaped blender mixer in a ratio of PEEK to hydroxyapatite of 90 wt %:10 wt % to be sufficiently and evenly mixed to prepare a dense layer powder material; $Na_2CO_3$ particles having a size of 600±m, PEEK powder having a grain size of 70 μm and hydroxyapatite of 70 nm are sufficiently mixed for 30 min with a planet ball mill at a rotation speed of 200 rpm in a ratio of PEEK to $Na_2CO_3$ to hydroxyapatite of 65 wt %:25 wt %:10 wt % to prepare a loose layer mixed powder material;

preparation of a cold pressed sheet: the dense layer powder material is paved at the bottom of the mould, the loose layer powder material is placed in the middle of the mould, the dense layer powder material is paved on the upper layer, the ready mould is placed in a hydraulic machine to compact the materials at a pressure of 40 MPa, pressurizing and pressure releasing are repeatedly carried out three times, the pressure is gradually raised when in pressurizing so that the residual gas in the mould is discharged, and the pressure is maintained for 5 min when achieving 40 Mpa, so as to ensure the quality and property of the product;

melting: the cold pressed mould is placed on a high-temperature oven or an external heating device for melting and heating the material, wherein, the temperature is set as 400° C., and heating time is 1 h;

hot pressing: the mould in which the material is completely molten is quickly placed into a hydraulic machine for hot pressing, with a set pressure of 20 MPa; pressurizing and pressure releasing are repeatedly carried out three times, the pressure is gradually raised when in pressurizing, and the pressure is maintained for 10 min after achieving 20 Mpa;

cooling: the pressure is released from the press machine when the temperature is reduced to less than 300° C. after the pressure is maintained, and the mould is cooled at a speed of 40° C./min; and demoulding: when the temperature of the mould is reduced to less than 150° C., a board is demoulded and taken out; the structure of the board is as shown in FIG. 1, wherein, the inner and outer dense layers are both provided with blind hole structures whose pore size is 2 mm and a gap is 4 mm; the loose layer has three-dimensional pores with a pore size of 600 μm and a porosity of 25%; the thicknesses of the inner and outer dense layers are 1 mm, and the thickness of the loose layer is 2 mm.

3. Plastic treatment: the built three-dimensional model for the skull defect part of the patient is guided into moldless multi-point molding equipment, the demouded blank obtained in the above step is heated to 200° C., the heated blank is quickly transferred to the moldless multi-point molding equipment, compression molding is carried out to obtain the personalized skull repairing prosthesis customized according to the patient, and the skull repairing prosthesis is cut so that its size exceeds the size of the calculated artificial skull by about 1 cm.

4. Preparation of a personalized porous bionic skull repairing prosthesis: the personalized skull repairing prosthesis obtained in the above step is placed into an ultrasonic water bath pot with a set temperature of 80° C. until the porogen is completely separated out, and subsequently, drying is carried out (about 24 h).

5. Antibiotic tobramycin is loaded into the pores of the dried personalized porous bionic skull repairing prosthesis in step 4 utilizing an embedding method to form a personalized porous bionic skull repairing prosthesis having an antibacterial function.

a. Mechanical Property Test

The porous bionic skull repairing prosthesis having the antibacterial function obtained in step 5 is tested according to a method stipulated by GB/T1040.1-2006. Results are as follows:

| Yield strength (MPa) | Elongation ratio at breaking (%) | Elasticity modulus (GPa) |
|---|---|---|
| 81 | 9.8 | 2.4 |

Example 5

1. A skull of a patient is scanned by using a computed tomography technology, a scanned image is stored in a DICOM (Digital Imaging and Communication in Medicine) format, data is divided and extracted utilizing image processing software, a three-dimensional model for a skull and a defect part of a patient is rebuilt, and the size and curvature of the artificial skull of the defect part are calculated.

2. Preparation of a board:

preparation of mixed powder: in the loose layer, a wound magnesium wire is selected as a porogen, various raw materials are weighed in a ratio of polyaryletheretherketone (PEEK) to nano hydroxyapatite to the porogen of 80 wt %:5 wt %:15 wt %, polyaryletheretherketone (PEEK) and nano hydroxyapatite are added into a V-shaped blender mixer to be sufficiently and evenly mixed to prepare a loose layer mixed powder material;

cold press molding: when in cold pressing, pure PEEK powder is added at the bottom of the mould for cold pressing to form a board, namely, an outer dense layer, then a wound magnesium wire is placed on the outer dense layer board, wherein, the diameter of the magnesium wire is 0.6 mm; the loose layer mixed powder material prepared in the above step is poured into the mould for pressing to form a loose layer, and finally, the pure PEEK powder is added on the loose layer, and pressurizing and pressure releasing are repeatedly carried out more than three times so as to prepare the cold pressed board, wherein, the pressure is set as 30 Mpa when in cold pressing, the pressure is gradually raised when in pressurizing, and the pressure is maintained for 5 min after achieving 30 Mpa;

melting: the board obtained in the above step and the mould are integrally put into an external heating device, wherein, the temperature is heated to 390° C., and heating time is 1 h;

hot press molding: the molten blank obtained in the above step is quickly placed into a press machine, pressurizing and pressure releasing are repeatedly carried out more than three times, the pressure is gradually raised when in pressurizing, and the pressure is maintained for 10 min after achieving 15 Mpa, and the blank is demoulded and taken out when the temperature is reduced to 150° C.; the structure of the board is as shown in FIG. 1, wherein, the inner and outer dense layers are both provided with blind hole structures whose pore size is 5 mm and a gap is 5 mm; the loose layer has three-dimensional pores with a pore size of 600 μm and a porosity of 15%; the thicknesses of the inner and outer dense layers are 1.5 mm, and the thickness of the loose layer is 2 mm.

3. Plastic treatment: the built three-dimensional model for the skull defect part of the patient is guided into moldless multi-point molding equipment, the blank obtained in the above step is heated to 200° C., the heated blank is quickly transferred to the moldless multi-point molding equipment, compression molding is carried out so as to obtain the personalized skull repairing prosthesis customized according to the patient, and the skull repairing prosthesis is cut so that its size exceeds the size of calculated artificial skull by about 1 cm.

4. Preparation of a personalized porous bionic skull repairing prosthesis: the personalized skull repairing prosthesis obtained in the above step is placed into hydrochloric acid until the porogen is completely corroded, subsequently, the personalized skull repairing prosthesis is placed into an ultrasonic water bath pot to be sufficiently soaked to remove strong acid, and then drying is carried out (for about 24 h) to obtain the porous bionic skull repairing prosthesis customized according to the patient.

a. Mechanical Property Test

The porous bionic skull repairing prosthesis obtained in step 4 is tested according to a method stipulated by GB/T1040.1-2006. Results are as follows:

| Yield strength (MPa) | Elongation ratio at breaking (%) | Elasticity modulus (GPa) |
|---|---|---|
| 76 | 9.4 | 2.3 |

Example 6

The porous bionic skull repairing prosthesis is prepared according to the method in Example 1, and a difference is that the loose layer is a mixture of PEEK powder having a grain size of 70 μm and NaCl powder having a grain size of 500±m in a ratio of PEEK to NaCl of 20 wt %:80 wt %. The loose layer of the obtained porous bionic skull repairing prosthesis has three-dimensional pores with a pore size of 500 μm and a porosity of 80%.

Example 7

The porous bionic skull repairing prosthesis is prepared according to the method in Example 2, and a difference is that the loose layer is a mixture of NaCl particles having a grain size of 600 μm, PEEK powder having a grain size of 70 μm and hydroxyapatite having a grain size of 70 nm in a ratio of PEEK to NaCl to hydroxyapatite of 20 wt %:70 wt %:10 wt %. The loose layer of the obtained porous bionic skull repairing prosthesis has three-dimensional pores with a pore size of 600 μm and porosity of 70%.

Example 8

The personalized porous bionic skull repairing prosthesis having an antibacterial function is prepared according to the method in Example 4, and a difference is that the loose layer is a mixture of Na$_2$CO$_3$ particles having a grain size of 600 μm, PEEK powder having a grain size of 70 μm and hydroxyapatite having a grain size of 70 nm in a ratio of PEEK to Na$_2$CO$_3$ to hydroxyapatite of 25 wt %:65 wt %:10 wt %. The loose layer of the obtained porous bionic skull repairing prosthesis has three-dimensional pores with a pore size of 600 μm and a porosity of 65%.

Example 9

The personalized porous bionic skull repairing prosthesis having an antibacterial function is prepared according to the method in Example 5, and a difference is that the loose layer is a mixture of a wound magnesium wire having a diameter of 600±m, PEEK powder having a grain size of 70 μm and hydroxyapatite having a grain size of 70 nm in a ratio of PEEK to a magnesium wire to hydroxyapatite of 15 wt %:80 wt %:5 wt %. The loose layer of the obtained porous bionic skull repairing prosthesis has three-dimensional pores with a pore size of 600 μm and porosity of 80%.

What is claimed is:

1. A porous bionic skull repairing material, from inner to outer, successively comprising an inner dense layer, a loose layer and an outer dense layer, wherein the loose layer is located between the inner dense layer and the outer dense layer, and the inner dense layer and the outer dense layer are both connected with the loose layer,
    wherein the inner dense layer and the outer dense layer are both provided with asymmetrical blind hole structures; wherein, a diameter of each of the blind hole structures is 0.1 mm-10 mm, a gap between the blind hole structures is 1 mm-10 mm; the loose layer is of a porous structure with a pore size of 10-700 μm and a porosity of 5%-90%.

2. The porous bionic skull repairing material according to claim 1, wherein the porous structure of the loose layer is a three-dimensional porous structure or a crossed pore-shaped structure.

3. The porous bionic skull repairing material according to claim 1, wherein the inner dense layer and the outer dense layer simulate a cortical bone structure, and the loose layer simulates a skull bone trabecula structure.

4. The porous bionic skull repairing material according to claim 1, wherein the porous bionic skull repairing material is configured to match with a human skull structure.

5. The porous bionic skull repairing material according to claim 1, wherein the inner dense layer and the outer dense layer are made of polymer materials, or made of a polymer material and a bioactive substance, and the materials of the inner dense layer and the outer dense layer can be the same or different, wherein, the polymer material is a non-degradable polymer material or a degradable polymer material; the loose layer is made of a polymer material and a porogen, or made of a polymer material, a porogen and a bioactive substance, wherein, the polymer material is a non-degradable polymer material or a degradable polymer material.

6. The porous bionic skull repairing material according to claim 5, wherein the porogen is an inorganic salt forming a three-dimensional porous structure or a metal wire forming a crossed pore-shaped structure,
    wherein a positive ion of the inorganic salt is a sodium ion or a potassium ion, a negative ion is at least one of a chloride ion, a carbonate ion, a sulfate ion, a phosphate ion and a nitrate ion, wherein the inorganic salt is at least one of sodium chloride, sodium carbonate, potassium chloride, potassium sulfate, potassium carbonate and potassium phosphate,
    wherein the metal wire is formed by winding at least one of a magnesium wire, a zinc wire and an aluminum wire.

7. The porous bionic skull repairing material according to claim 5, wherein the non-degradable polymer material is a polyaryletherketone material, comprising at least one of polyetheretherketone (PEEK), polyetherketone (PEK), polyetherketoneketone (PEKK), polyetheretherketoneketone (PEEKK) and polyetherketoneetherketoneketone (PEKEKK);
    wherein the degradable polymer material is a polyester degradable polymer material comprising at least one of polylactic acid, polyglycollide and polycaprolactone;
    wherein the bioactive substance is at least one of nano hydroxyapatite (HAp), nano titania (TiO$_2$), calcium silicate, β-tricalcium phosphate and bioactive glass.

8. The porous bionic skull repairing material according to claim 1, wherein at least one of the inner dense layer, the outer dense layer and the loose layer contains an antibiotic component or an active factor; when being present in the inner dense layer or the outer dense layer, the antibiotic component or the active factor are located on the naked surface of the inner dense layer or the outer dense layer; when being present in the loose layer, the antibiotic component or/and the active factor are located on the naked surface of the loose layer and in the pores inside the loose layer.

9. The porous bionic skull repairing material according to claim 8, wherein the antibiotic component is at least one of a metal substance, a non-metal substance and an organic substance, the metal substance is at least one of a silver ion, a zinc ion, a copper ion, silver oxide, zinc oxide and copper oxide, the non-metal substance is a compound containing at least one of a hydrogen element, a chlorine element and a selenium element and having an antibacterial action, the organic substance is at least one of antibiotics, antimicrobial peptide and chitosan; the active factor is at least one of a bone Gla protein (BGP), a bone morphogenetic protein (BMP) and a basic fibroblast growth factor (BFGF).

10. The porous bionic skull repairing material according to claim 1, wherein the porous bionic skull repairing material is subjected to surface modification by virtue of one or more of the following a-g manners:
    a. treating the porous bionic skull repairing material with a gas cluster ion beam method;
    b. treating the porous bionic skull repairing material with a plasma method;
    c. treating the porous bionic skull repairing material with a surface covering method;
    d. treating the porous bionic skull repairing material with a laser irradiation method;
    e. treating the porous bionic skull repairing material with an electron beam deposition method;
    f. treating the porous bionic skull repairing material with an embedding method; and
    g. treating the porous bionic skull repairing material with an osmose method.

11. The porous bionic skull repairing material according to claim 1, wherein the porous bionic skull repairing material is prepared by using a 3D printing technology or a mixed mould pressing method.

* * * * *